(12) United States Patent
Novak et al.

(10) Patent No.: US 8,685,677 B2
(45) Date of Patent: Apr. 1, 2014

(54) DETECTION OF AAD-12 SOYBEAN EVENT 416

(75) Inventors: Stephen Novak, Westfield, IN (US); Yunxing C. Cui, Carmel, IN (US); Thomas W. Greene, West Des Moines, IA (US); Ning Zhou, Zionsville, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/511,995

(22) PCT Filed: Nov. 24, 2010

(86) PCT No.: PCT/US2010/057967
§ 371 (c)(1),
(2), (4) Date: Oct. 8, 2012

(87) PCT Pub. No.: WO2011/066360
PCT Pub. Date: Jun. 3, 2011

(65) Prior Publication Data
US 2013/0029329 A1    Jan. 31, 2013

Related U.S. Application Data

(60) Provisional application No. 61/327,369, filed on Apr. 23, 2010, provisional application No. 61/263,950, filed on Nov. 24, 2009.

(51) Int. Cl.
*C12P 19/34* (2006.01)
(52) U.S. Cl.
USPC ........................................................ 435/91.2
(58) Field of Classification Search
USPC ........................................................ 435/91.2
See application file for complete search history.

(56) References Cited

U.S. PATENT DOCUMENTS

2006/0127889 A1    6/2006  Dotson et al.

FOREIGN PATENT DOCUMENTS

WO    WO 2007/053482 A2    5/2007

OTHER PUBLICATIONS

GenBank Accession No. EW881694. Created Aug. 24, 2007. [online], [retrieved on Feb. 22, 2011. Retrieved from the internet, URL:http://www.ncbi.nlm.nih.gov/nucest/EW881694>.
Schmidt, et al., Quantitative detection of transgenes in soybean (*Glycine max* (L.) Merrill] and peanut (*Arachis hypogaea* L.) by real-time polymerase chain reaction. Plant Cell Resp. 2001, vol. 20, pp. 442-428.

*Primary Examiner* — Cynthia B Wilder
(74) *Attorney, Agent, or Firm* — Ronald S. Maciak; Faegre Baker Daniels LLP

(57) ABSTRACT

The invention relates in part to methods of detecting an AAD-12 soybean event. The subject invention provides assays for detecting the presence of the subject event in a sample (of soybeans, for example). Kits and conditions useful in conducting the assays are also provided. More specifically, the present invention relates in part to an endpoint TaqMan PCR assay for the AAD-12 soybean event. Some embodiments are directed to assays that are capable of high throughput zygosity analysis. The subject invention further relates, in part, to the discovery of a preferred reference gene for use in determining zygosity. This invention also relates in part to plant breeding using any of the subject methods. In some embodiments, said event/polynucleotide sequence can be "stacked" with other traits. The subject procedures can be used to uniquely identify soybean lines comprising the event of the subject invention.

19 Claims, 4 Drawing Sheets

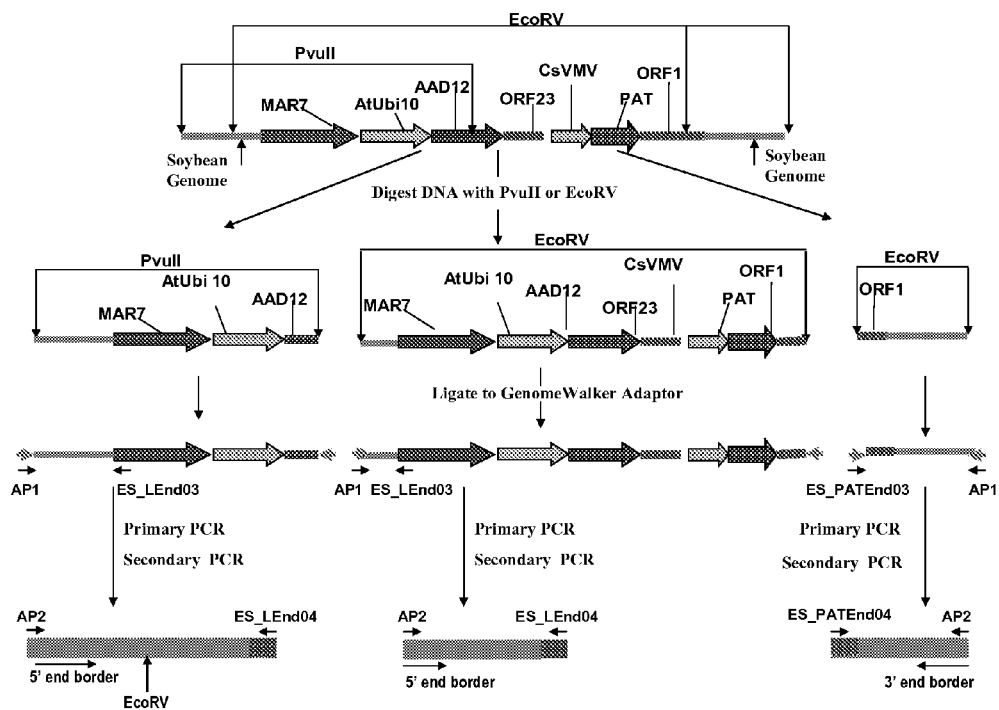
Figure 1. Genomic DNA of the soybean event DAS-68416-4 was digested with EcoRV, or Pvu II and used to generate corresponding GENOMEWALKER™ libraries, which were used as templates to amplify the target DNA sequences.

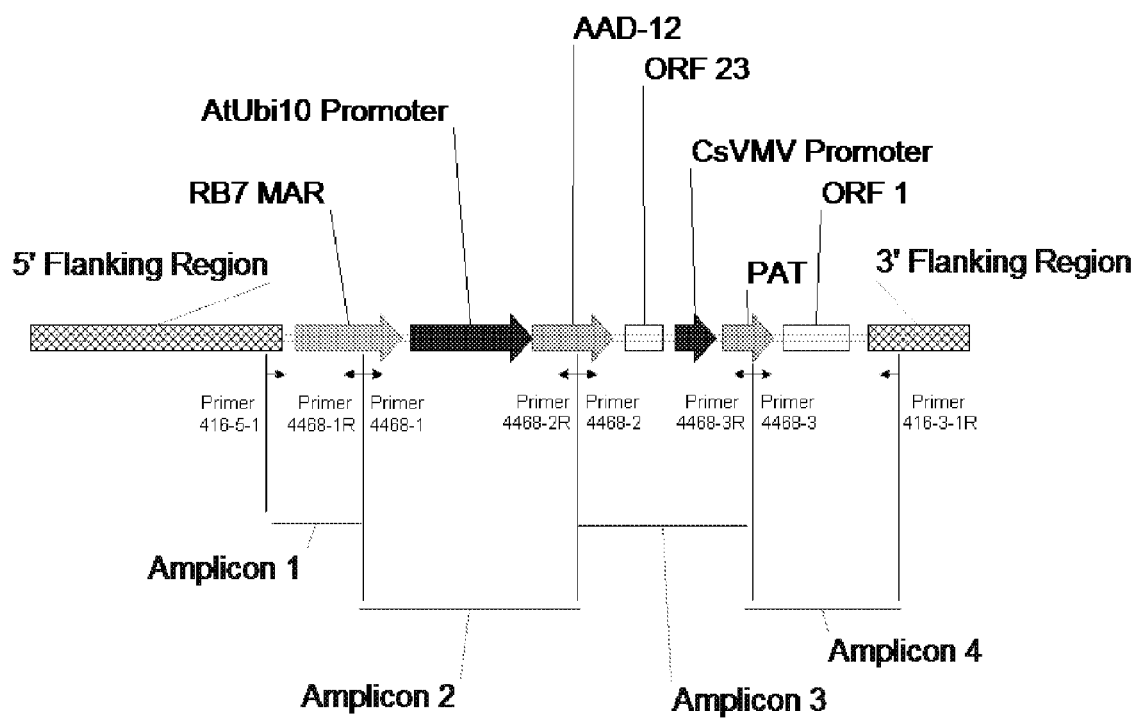
Figure 2. The schematic diagram depicts the primer locations and cloning strategy for full length sequencing of the soybean Event DAS-68416-4 from 5' to 3' borders.

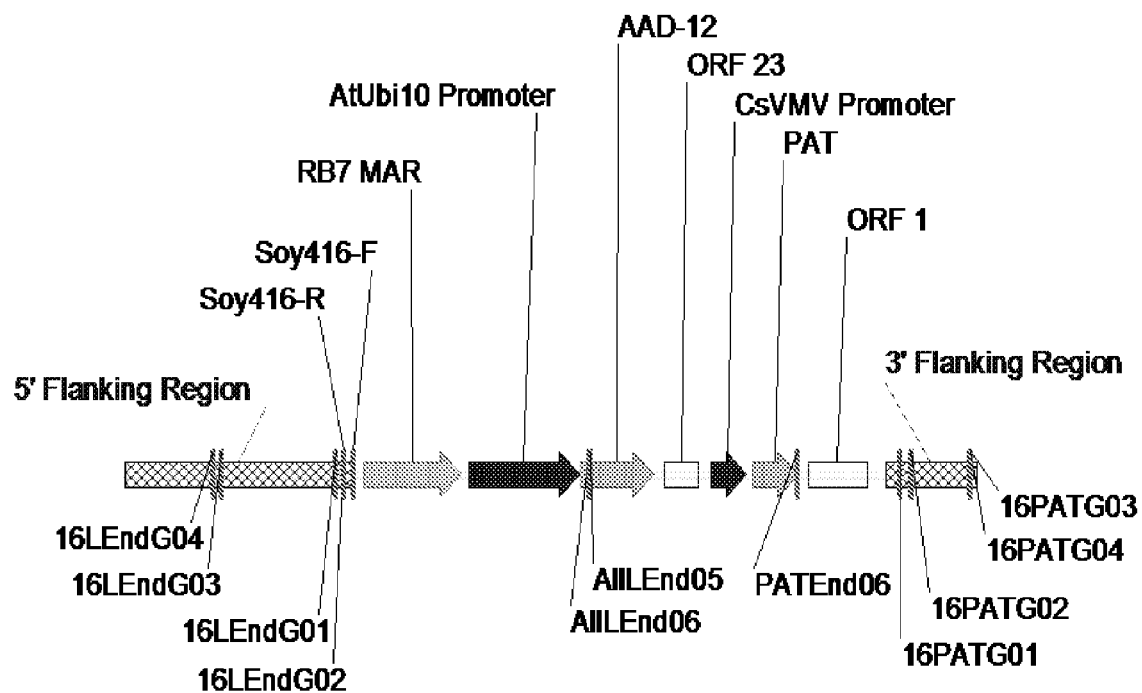
Figure 3. The schematic diagram depicts the primer locations for confirming the full length sequence of the soybean Event DAS-68416-4 from 5' to 3' borders.

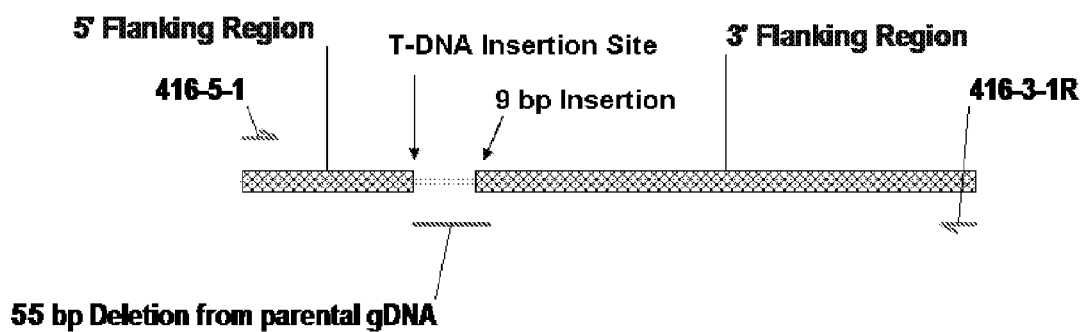
Figure 4. The schematic diagram depicts the primer locations for confirming the insertion site sequence of the AAD-12 soybean event DAS-68416-4.

DETECTION OF AAD-12 SOYBEAN EVENT 416

CROSS-REFERENCE TO RELATED APPLICATIONS

This application is a national phase application, filed pursuant to 35 U.S.C. §371, of PCT application No. PCT/US2010/057967, filed on Nov. 24, 2010, which claims the benefit of U.S. Provisional application No. 61/263,950, filed on Nov. 24, 2009, and U.S. Provisional application No. 61/327,369, filed on Apr. 23, 2010. The prior applications are incorporated herein by reference in their entirety.

REFERENCE TO SEQUENCE LISTING SUBMITTED VIA EFS-WEB

The instant application contains a Sequence Listing which has been submitted via EFS-Web and is hereby incorporated by reference in its entirety. The Sequence Listing is provided as a text file named DAS-P0170-03-US_9255138_1.TXT. The size of the text file containing the Sequence Listing is 14898 bytes and was created Oct. 8, 2012.

BACKGROUND OF THE INVENTION

The aad-12 gene (originally from *Delftia acidovorans*) encodes the aryloxyalkanoate dioxygenase (AAD-12) protein. The trait confers tolerance to 2,4-dichlorophenoxyacetic acid, for example, and to pyridyloxyacetate herbicides. The aad-12 gene, itself, for herbicide tolerance in plants was first disclosed in WO 2007/053482.

The expression of heterologous or foreign genes in plants is influenced by where the foreign gene is inserted in the chromosome. This could be due to chromatin structure (e.g., heterochromatin) or the proximity of transcriptional regulation elements (e.g., enhancers) close to the integration site (Weising et al., *Ann. Rev. Genet* 22:421-477, 1988), for example. The same gene in the same type of transgenic plant (or other organism) can exhibit a wide variation in expression level amongst different events. There may also be differences in spatial or temporal patterns of expression. For example, differences in the relative expression of a transgene in various plant tissues may not correspond to the patterns expected from transcriptional regulatory elements present in the introduced gene construct.

Thus, large numbers of events are often created and screened in order to identify an event that expresses an introduced gene of interest to a satisfactory level for a given purpose. For commercial purposes, it is common to produce hundreds to thousands of different events and to screen those events for a single event that has desired transgene expression levels and patterns. An event that has desired levels and/or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

Various prior methods can be used to detect the presence of an event in a sample of plant tissue. One example is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene insert/flanking sequence due to successful amplification, hybridization, and single or multi-base extension. (This technique is usually used for initial sequencing, not for detection of a specific gene when it is known.)

Fluorescence Polarization is another method that can be used to detect an amplicon. Following this method, an oligonucleotide is designed to overlap the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

Molecular Beacons have been described for use in sequence detection. Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal indicates the presence of the flanking genomic/transgene insert sequence due to successful amplification and hybridization.

Hydrolysis probe assay, otherwise known as TAQMAN (Life Technologies, Foster City, Calif.), is a method of detecting and quantifying the presence of a DNA sequence. Briefly, a FRET oligonucleotide probe is designed with one oligo within the transgene and one in the flanking genomic sequence for event-specific detection. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Another challenge, among many, is finding a suitable reference gene for a given test. For example, as stated in the abstract of Czechowski et al., "An exceptionally large set of data from Affymetrix ATH1 whole-genome GeneChip studies provided the means to identify a new generation of reference genes with very stable expression levels in the model plant species *Arabidopsis* (*Arabidopsis thaliana*). Hundreds of *Arabidopsis* genes were found that outperform traditional reference genes in terms of expression stability throughout development and under a range of environmental conditions." (Czechowski et al. (2005) Genome-wide identification and testing of superior reference genes for transcript normalization in *Arabidopsis*. *Plant Physiol.* 139, 5-17.)

Brodmann et al. (2002) relates to real-time quantitative PCR detection of transgenic maize content in food for four different maize varieties approved in the European Union. Brodmann, P. D., P. D., Ilg E. C., Berthoud H., and Herrmann, A. Real-Time Quantitative Polymerase Chain Reaction Methods for Four Genetically Modified Maize Varieties and Maize DNA Content in Food. *J. of AOAC international* 2002 85 (3)

Hernandez et al. (2004) mentions four possible genes for use with real-time PCR. Hernandez, M., Duplan, M.-N., Berthier, G., Vaitilingom, M., Hauser, W., Freyer, R., Pla, M., and Bertheau, Y. Development and comparison of four real-time polymerase chain reaction systems for specific detection and quantification of *Zea mays* L. *J. Agric. Food Chem.* 2004, 52, 4632-4637.

Costa et al. (2007) looked at these four genes (also in the real-time PCR context) and concluded that the alcohol dehydrogenase and zein genes were the best reference genes for detecting a sample "event" (a lectin gene) for transgenic feed intermix issues. Costa, L. D., and Martinelli L. Development of a Real-Time PCR Method Based on Duplo Target Plasmids for Determining an Unexpected Genetically Modified Soybean Intermix with Feed Components. *J. Agric. Food Chem.* 2007, 55, 1264-1273.

Huang et al. (2004) used plasmid pMulM2 as reference molecules for detection of MON810 and NK603 transgenes in maize. Huang and Pan, "Detection of Genetically Modified Maize MON810 and NK603 by Multiplex and Real-Time Polymerase Chain Reaction Methods," *J. Agric. Food Chem.*, 2004, 52 (11), pp 3264-3268.

Gasparic et al. (2008) suggest LNA technology, from a comparison to cycling probe technology, TaqMan, and various real-time PCR chemistries, for quantitatively analyzing maize events (such as MON810). Gašparič, Cankar, Žel, and Gruden, "Comparison of different real-time PCR chemistries and their suitability for detection and quantification of genetically modified organisms," BMC Biotechnol. 2008; 8: 26.

US 20070148646 relates to a primer extension method for quantification that requires controlled dispensation of individual nucleotides that can be detected and quantified by the amount of nucleotides incorporated. This is different from the TaqMan PCR method using an internal reference gene.

To distinguish between homozygous and hemizygous genotypes of TC1507, an Invader assay has been successfully used for this event. Gupta, M., Nirunsuksiri, W., Schulenberg, G., Hartl, T., Novak, S., Bryan, J., Vanopdorp, N., Bing, J. and Thompson, S. A non-PCR-based Invader Assay Quantitatively Detects Single-Copy Genes in Complex Plant Genomes. Mol. Breeding 2008, 21, 173-181.

Huabang (2009) relates to PCR-based zygosity testing of transgenic maize. However, no reference gene appears to be used. Huabang, "An Accurate and Rapid PCR-Based Zygosity Testing Method for Genetically Modified Maize," Molecular Plant Breeding, 2009, Vol. 7, No. 3, 619-623.

BRIEF SUMMARY OF THE INVENTION

The present invention is related in part to methods of detecting the AAD-12 soybean (*Glycine max*) event designated DAS-68416-4 having seed deposited with American Type Culture Collection (ATCC) with Accession No. PTA-10442.

More specifically, the present invention relates in part to endpoint TaqMan PCR assays for the AAD-12 soybean event. Some embodiments are directed to assays that are capable of high throughput zygosity analysis. The subject invention further relates, in part, to the discovery of a preferred lectin reference gene for use in determining zygosity. These and other related procedures can be used to uniquely identify soybean lines comprising the event of the subject invention.

This invention also relates in part to plant breeding using any of the subject methods. In some embodiments, said event/polynucleotide sequence can be "stacked" with other traits, including, for example, other herbicide tolerance gene(s) and/or insect-inhibitory proteins. However, the subject invention includes plants having the single event, as described herein.

Additionally, the subject invention provides assays for detecting the presence of the subject event in a sample (of soybeans, for example). Kits and conditions useful in conducting the assays are also provided.

BRIEF DESCRIPTION OF THE FIGURES

FIG. 1. Genomic DNA of the soybean event DAS-68416-4 was digested with EcoRV, or Pvu II and used to generate corresponding GENOMEWALKER™ libraries, which were used as templates to amplify the target DNA sequences.

FIG. 2. The schematic diagram depicts the primer locations and cloning strategy for full length sequencing of the soybean Event DAS-68416-4 from 5' to 3' borders.

FIG. 3. The schematic diagram depicts the primer locations for confirming the full length sequence of the soybean Event DAS-68416-4 from 5' to 3' borders.

FIG. 4. The schematic diagram depicts the primer locations for confirming the insertion site sequence of the AAD-12 soybean event DAS-68416-4.

BRIEF DESCRIPTION OF THE SEQUENCES

SEQ ID NO:1 provides a sequence of 5' and 3' genomic flanking sequences on either side of the AAD-12 insert, including the insert. The flanking sequences are underlined.

SEQ ID NOS:2-7 provide sequences for primers and probes for use according to the subject invention.

DETAILED DESCRIPTION OF THE INVENTION

Transgenic AAD-12 (providing herbicide tolerance) soybean event pDAB4468-416 was generated by *Agrobacterium* transformation. Both 5' and 3' end flanking sequences of this AAD-12 transgene insert were cloned, sequenced, and characterized as detailed in U.S. Ser. No. 61/263,950 (filed Nov. 24, 2009). In some specific embodiments, the AAD-12 is present in soybeans as the event designated DAS-68416-4 having seed deposited with American Type Culture Collection (ATCC), Manassas; Va. 20110 U.S.A., with Accession No. PTA-10442, and progeny derived thereof 2500 seeds of AAD-12 Event pDAB4468-0416 (ATCC Accession No. PTA-10442) were deposited in accordance with the Budapest Treaty on Oct. 22, 2009. The deposit was tested on Nov. 2, 2009, and on that date, the seeds were viable.

Specific TAQMAN primers and probe were designed, as detailed herein, in part according to the DNA sequences located in the junction region between the transgene and the host genomic DNA. Event specificity of the primers and probe was successfully tested in duplex format with the soybean Lectin as a reference gene in real time PCR against different AAD-12 soybean events and non-transgenic soybean variety Maverick. Procedures for end-point event specific TAQMAN assays for the AAD-12 soybean event were developed, as detailed herein.

The sequence spanning the region of the intergration junction between host plant DNA and the integrated gene construct in this AAD-12 soybean event is a unique sequence. It was used to develop event specific assays (conventional PCR or real time PCR) to detect presence of AAD-12 soybean Event pDAB4468-416 for GMO testing and to determine zygosity status of plants in breeding populations. The event-specific TAQMAN assay reported herein can be employed for both applications.

The subject invention provides assays for detecting the presence of transgenic soybean event DAS-68416-4 in a sample. Aspects of the subject invention include methods of designing and/or producing any diagnostic nucleic acid molecules exemplified or suggested herein. Plant lines comprising this event can be detected using sequences disclosed and suggested herein.

Thus, in some embodiments, this invention relates to the identification of herbicide-tolerant soybean lines. The subject invention relates in part to detecting the presence of the subject event in order to determine whether progeny of a sexual cross contain the event of interest. In addition, a method for detecting the event is included and is helpful, for example, for complying with regulations requiring the pre-market approval and labeling of foods derived from recombinant crop plants, for example.

More specifically, the event is an AAD-12 event also called pDAB4468-0416. This invention can be used for its selection and characterization for stability and expression at whole plant and molecular levels from generation to generation.

The subject synthetic gene (aad-12) used according to the subject invention was derived from *Delftia acidovorans* and encodes an enzyme capable of deactivating several herbicides with an aryloxyalkanoate moiety, including phenoxy auxin (e.g., 2,4-D, MCPA), as well as pyridyloxy auxins (e.g., fluroxypyr, triclopyr). The aad-12 gene, driven by atUbi10 promoters, was introduced into the soybean line Maverick via *Agrobacterium tumefaciens* techniques.

The subject invention relates in part to a fluorescence-based endpoint TaqMan PCR assay utilizing an endogenous gene as a reference (copy number) control for high-throughput zygosity analysis of the AAD-12 soybean event. The subject invention further relates, in part, to the discovery of a preferred reference gene, invertase. Several reference genes were identified as possible options.

The subject invention also relates in part to the development of a biplex endpoint TaqMan PCR for AAD-12 soybean event specific zygosity analysis. Further, the subject invention relates in part to the development of AAD-12 breeding test kits.

Endpoint TaqMan assays are based on a plus/minus strategy, by which a "plus" signifies the sample is positive for the assayed gene and a "minus" signifies the sample is negative for the assayed gene. These assays typically utilize two sets of oligonucleotides for identifying the AAD-12 transgene sequence and the wild-type gene sequence respectively, as well as dual-labeled probes to measure the content of transgene and wild type sequence.

Although the Invader assay has been a robust technique for characterizing events, it is very sensitive to DNA quality. In addition, the assay requires a high quantity of DNA. Invader also requires an additional denaturing step which, if not handled properly, can render the Invader assay unsuccessful. Additionally, the longer assay time of the Invader assay is limited in its flexibility to efficiently handle large numbers of AAD-12 event 416 samples for analysis in a commercial setting. One main advantage of the subject invention is time savings and elimination of the denaturing step.

The subject Endpoint TaqMan analysis for detecting AAD-12 416 events offers surprising advantages over Invader, particularly in analyzing large number of samples.

Definitions and examples are provided herein to help describe the present invention and to guide those of ordinary skill in the art to practice the invention. Unless otherwise noted, terms are to be understood according to conventional usage by those of ordinary skill in the relevant art. The nomenclature for DNA bases as set forth at 37 CFR §1.822 is used.

As used herein, the term "progeny" denotes the offspring of any generation of a parent plat which comprises AAD-12 soybean event DAS-68416-4.

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

A "junction sequence" spans the point at which DNA inserted into the genome is linked to DNA from the soybean native genome flanking the insertion point, the identification or detection of one or the other junction sequences in a plant's genetic material being sufficient to be diagnostic for the event. Included are the DNA sequences that span the insertions in herein-described soybean events and similar lengths of flanking DNA. Specific examples of such diagnostic sequences are provided herein; however, other sequences that overlap the junctions of the insertions, or the junctions of the insertions and the genomic sequence, are also diagnostic and could be used according to the subject invention.

The subject invention relates to the identification of such flanking, junction, and insert sequences. Related PCR primers and amplicons are included in the invention. According to the subject invention, PCR analysis methods using amplicons that span across inserted DNA and its borders can be used to detect or identify commercialized transgenic soybean varieties or lines derived from the subject proprietary transgenic soybean lines.

The entire sequences of each of these inserts, together with portions of the respective flanking sequences, are provided herein as SEQ ID NO:1. The coordinates of the insert and flanking sequences for this event with respect to SEQ ID NO:1 (10,212 basepairs total) are indicated below.

|  | 5' Flanking | Insert | 3' Flanking |
| --- | --- | --- | --- |
| residue #s (SEQ: 1): | 1-2730 | 2731-9121 | 9122-10,212 |
| length (bp): | 2730 bp | 6391 bp | 1091 bp |

The components of the insert and flanking sequences are further illustrated in FIGS. 1 through 4.

Detection techniques of the subject invention are especially useful in conjunction with plant breeding, to determine which progeny plants comprise a given event, after a parent plant comprising an event of interest is crossed with another plant line in an effort to impart one or more additional traits of interest in the progeny. These analysis methods benefit soybean breeding programs as well as quality control, especially for commercialized transgenic soybeanseeds. Detection kits for these transgenic soybean lines can also now be made and used. This can also benefit product registration and product stewardship. These can be used for accelerated breeding strategies and to establish linkage data.

Sequences provided herein can be used to study and characterize transgene integration processes, genomic integration site characteristics, event sorting, stability of transgenes and their flanking sequences, and gene expression (especially related to gene silencing, transgene methylation patterns, position effects, and potential expression-related elements such as MARS [matrix attachment regions], and the like).

Still further, the subject invention includes selection of descendant and/or progeny plants, preferably a herbicide-resistant soybean plant wherein said plant has a genome comprising a detectable DNA insert as described herein. As used herein, the term "soybean" means *Glycine max* and includes all varieties thereof that can be bred with a soybean plant.

This invention further includes processes of making crosses using a plant of the subject invention as at least one parent. This invention includes a method for producing an $F_1$ hybrid seed by crossing an exemplified plant with a different (e.g. in-bred parent) plant and harvesting the resultant hybrid seed. Characteristics of the resulting plants (either a female) may be improved by careful consideration of the parent plants.

A herbicide-tolerant soybean plant can be bred by first sexually crossing a first parental soybean plant consisting of a soybean plant grown from seed of any one of the lines referred to herein, and a second parental soybean plant, thereby producing a plurality of first progeny plants; and then selecting a first progeny plant that is resistant to a herbicide (or that possesses at least one of the events of the subject invention); and selfing the first progeny plant, thereby producing a plurality of second progeny plants; and then selecting from the second progeny plants a plant that is resistant to a herbicide (or that possesses at least one of the events of the subject invention). These steps can further include the back-crossing of the first progeny plant or the second progeny plant to the second parental soybean plant or a third parental soybean plant. A soybean crop comprising soybean seeds of the subject invention, or progeny thereof, can then be planted.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Other breeding methods commonly used for different traits and crops are known in the art. Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (back-crossed) to the recurrent parent. The resulting parent is expected to have the attributes of the recurrent parent (e.g., cultivar) and the desirable trait transferred from the donor parent.

The present invention can be used with molecular markers in a marker assisted breeding (MAB) method. DNA molecules of the present invention can be used with other methods (such as, AFLP markers, RFLP markers, RAPD markers, SNPs, and SSRs) that identify genetically linked agronomically useful traits, as is known in the art. The herbicide-resistance trait can be tracked in the progeny of a cross with a soybean plant of the subject invention (or progeny thereof and any other soybean cultivar or variety) using the MAB methods. The DNA molecules are markers for this trait, and MAB methods that are well known in the art can be used to track the hebicide-resistance trait(s) in soybean plants where at least one soybean line of the subject invention, or progeny thereof, was a parent or ancestor. The methods of the present invention can be used to identify any soybean variety having the subject event.

Methods of the subject invention include a method of producing a herbicide-tolerant soybean plant wherein said method comprises breeding with a plant of the subject invention. More specifically, said methods can comprise crossing two plants of the subject invention, or one plant of the subject invention and any other plant. Preferred methods further comprise selecting progeny of said cross by analyzing said progeny for an event detectable according to the subject invention. For example, the subject invention can be used to track the subject event through breeding cycles with plants comprising other desirable traits, such as agronomic traits such as those tested herein in various Examples. Plants comprising the subject event and the desired trait can be detected, identified, selected, and quickly used in further rounds of breeding, for example. The subject event/trait can also be combined through breeding, and tracked according to the subject invention, with an insect resistant trait(s) and/or with further herbicide tolerance traits. One preferred embodiment of the latter is a plant comprising the subject event combined with a gene encoding resistance to the herbicide dicamba.

The subject event can be combined with, for example, traits encoding glyphosate resistance (e.g., resistant plant or bacterial EPSPS, GOX, GAT), glufosinate resistance (e.g., Pat, bar), acetolactate synthase (ALS)-inhibiting herbicide resistance (e.g., imidazolinones [such as imazethapyr], sulfonylureas, triazolopyrimidine sulfonanilide, pyrmidinylthiobenzoates, and other chemistries [Csr1, SurA, et al.]), bromoxynil resistance (e.g., Bxn), resistance to inhibitors of HPPD (4-hydroxlphenyl-pyruvate-dioxygenase) enzyme, resistance to inhibitors of phytoene desaturase (PDS), resistance to photosystem II inhibiting herbicides (e.g., psbA), resistance to photosystem I inhibiting herbicides, resistance to protoporphyrinogen oxidase IX (PPO)-inhibiting herbicides (e.g., PPO-1), resistance to phenylurea herbicides (e.g., CYP76B1), dicamba-degrading enzymes (see, e.g., US 20030135879), and others could be stacked alone or in multiple combinations to provide the ability to effectively control or prevent weed shifts and/or resistance to any herbicide of the aforementioned classes.

Regarding additional herbicides, some additional preferred ALS (also known as AHAS) inhibitors include the triazolopyrimidine sulfonanilides (such as cloransulam-methyl, diclosulam, florasulam, flumetsulam, metosulam, and penoxsulam), pyrimidinylthiobenzoates (such as bispyribac and pyrithiobac), and flucarbazone. Some preferred HPPD inhibitors include mesotrione, isoxaflutole, and sulcotrione.

Some preferred PPO inhibitors include flumiclorac, flumioxazin, flufenpyr, pyraflufen, fluthiacet, butafenacil, carfentrazone, sulfentrazone, and the diphenylethers (such as acifluorfen, fomesafen, lactofen, and oxyfluorfen).

Additionally, AAD-12 alone or stacked with one or more additional HTC traits can be stacked with one or more additional input (e.g., insect resistance, fungal resistance, or stress tolerance, et al.) or output (e.g., increased yield, improved oil profile, improved fiber quality, et al.) traits. Thus, the subject invention can be used to provide a complete agronomic package of improved crop quality with the ability to flexibly and cost effectively control any number of agronomic pests.

The subject AAD-12 enzyme enables transgenic expression resulting in tolerance to combinations of herbicides that would control nearly all broadleaf and grass weeds. AAD-12 can serve as an excellent herbicide tolerant crop (HTC) trait to stack with other HTC traits (e.g., glyphosate resistance, glufosinate resistance, imidazolinone resistance, bromoxynil resistance, et al.), and insect resistance traits (Cry1F, Cry1Ab, Cry 34/45, et al.) for example. Additionally, AAD-12 can serve as a selectable marker to aid in selection of primary transformants of plants genetically engineered with a second gene or group of genes.

HTC traits of the subject invention can be used in novel combinations with other HTC traits (including but not limited to glyphosate tolerance). These combinations of traits give rise to novel methods of controlling weed (and like) species, due to the newly acquired resistance or inherent tolerance to herbicides (e.g., glyphosate). Thus, in addition to the HTC traits, novel methods for controlling weeds using herbicides, for which herbicide tolerance was created by said enzyme in transgenic crops, are within the scope of the invention.

Additionally, glyphosate tolerant crops grown worldwide are prevalent. Many times in rotation with other glyphosate tolerant crops, control of glyphosate-resistant volunteers may be difficult in rotational crops. Thus, the use of the subject transgenic traits, stacked or transformed individually into crops, provides a tool for controlling other HTC volunteer crops.

Unless indicated otherwise, reference to flanking sequences refers to those identified with respect to SEQ ID NO:1 (see the Table above). Again, SEQ ID NO:1 includes the heterologous DNA inserted in the original transformant and illustrative flanking genomic sequences immediately adjacent to the inserted DNA. All or part of these flanking sequences could be expected to be transferred to progeny that receives the inserted DNA as a result of a sexual cross of a parental line that includes the event.

As used herein, a "line" is a group of plants that display little or no genetic variation between individuals for at least one trait. Such lines may be created by several generations of self-pollination and selection, or vegetative propagation from a single parent using tissue or cell culture techniques.

As used herein, the terms "cultivar" and "variety" are synonymous and refer to a line which is used for commercial production.

"Stability" or "stable" means that with respect to the given component, the component is maintained from generation to generation and, preferably, at least three generations at substantially the same level, e.g., preferably ±15%, more preferably ±10%, most preferably ±5%. The stability may be affected by temperature, location, stress and the time of planting. Comparison of subsequent generations under field conditions should produce the component in a similar manner.

"Commercial Utility" is defined as having good plant vigor and high fertility, such that the crop can be produced by farmers using conventional farming equipment, and the oil with the described components can be extracted from the seed using conventional crushing and extraction equipment. To be commercially useful, the yield, as measured by seed weight, oil content, and total oil produced per acre, is within 15% of the average yield of an otherwise comparable commercial soybean variety without the premium value traits grown in the same region.

"Agronomically elite" means that a line has desirable agronomic characteristics such as yield, maturity, disease resistance, and the like, in addition to the insect resistance due to the subject event(s). Agronomic traits, taken individually or in any combination, as set forth in Examples, below, in a plant comprising an event of the subject invention, are within the scope of the subject invention. Any and all of these agronomic characteristics and data points can be used to identify such plants, either as a point or at either end or both ends of a range of characteristics used to define such plants.

As one skilled in the art will recognize in light of this disclosure, preferred embodiments of detection kits, for example, can include probes and/or primers, including polynucleotide probes, and/or amplicons.

Primer(s) "touching down" in the flanking sequence are typically not designed to hybridize beyond about 200 bases or beyond the junction. Thus, typical flanking primers would be designed to comprise at least 15 residues of either strand within 200 bases into the flanking sequences from the beginning of the insert. That is, primers comprising a sequence of an appropriate size from (or hybridizing to) residues ~2530-2730 and/or ~9122-9322 of SEQ ID NO:1 are within the scope of the subject invention. Insert primers can likewise be designed anywhere on the insert, but residues ~2731-2931 and ~8921-9121, can be used, for example, non-exclusively for such primer design.

One skilled in the art will also recognize that primers and probes can be designed to hybridize, under a range of standard hybridization and/or PCR conditions, to a segment of SEQ ID NO:1 (or the complement), and complements thereof, wherein the primer or probe is not perfectly complementary to the exemplified sequence. That is, some degree of mismatch can be tolerated. For an approximately 20 nucleotide primer, for example, typically one or two or so nucleotides do not need to bind with the opposite strand if the mismatched base is internal or on the end of the primer that is opposite the amplicon. Various appropriate hybridization conditions are provided below. Synthetic nucleotide analogs, such as inosine, can also be used in probes. Peptide nucleic acid (PNA) probes, as well as DNA and RNA probes, can also be used. What is important is that such probes and primers are diagnostic for (able to uniquely identify and distinguish) the presence of an event of the subject invention.

Components of the "insert" are illustrated in the Figures. The DNA polynucleotide sequences of these components, or fragments thereof, can be used as DNA primers or probes in the methods of the present invention.

In some embodiments of the invention, compositions and methods are provided for detecting the presence of the transgene/genomic insertion region, in plants and seeds and the like, from a soybean plant. DNA sequences are provided, as well as segments thereof, and complements of the exemplified sequences and any segments thereof.

These and other related procedures can be used to uniquely identify these soybean lines.

In some embodiments, DNA sequences that comprise a contiguous fragment of the novel transgene/genomic insertion region are an aspect of this invention. Included are DNA sequences that comprise a sufficient length of polynucleotides of transgene insert sequence and a sufficient length of polynucleotides of soybean genomic sequence from one or more of the three aforementioned soybean plants and/or sequences that are useful as primer sequences for the production of an amplicon product diagnostic for one or more of these soybean plants.

Related embodiments pertain to DNA sequences that comprise at least 2, 3, 4, 5, 6, 7, 8, 9, 10, 11, 12, 13, 14, 15, 16, 17, 18, 19, 20, 21, 22, 23, 24, 25, or more contiguous nucleotides of a transgene portion of a DNA sequence identified herein (such as SEQ ID NO:1 and segments thereof), or complements thereof, and a similar length of flanking soybean DNA sequence from these sequences, or complements thereof. Such sequences are useful as DNA primers in DNA amplification methods. The amplicons produced using these primers are diagnostic for any of the soybean events referred to herein. Therefore, the invention also includes the amplicons produced by such DNA primers and homologous primers.

This invention also includes methods of detecting the presence of DNA, in a sample, that corresponds to the soybean event referred to herein. Such methods can comprise: (a) contacting the sample comprising DNA with a primer set that, when used in a nucleic acid amplification reaction with DNA from at least one of these soybean events, produces an amplicon that is diagnostic for said event(s); (b) performing a nucleic acid amplification reaction, thereby producing the amplicon; and (c) detecting the amplicon.

Further detection methods of the subject invention include a method of detecting the presence of a DNA, in a sample, corresponding to at least one of said events, wherein said method comprises: (a) contacting the sample comprising DNA with a probe that hybridizes under stringent hybridization conditions with DNA from at least one of said soybean events and which does not hybridize under the stringent hybridization conditions with a control soybean plant (non-event-of-interest DNA); (b) subjecting the sample and probe to stringent hybridization conditions; and (c) detecting hybridization of the probe to the DNA.

In still further embodiments, the subject invention includes methods of producing a soybean plant comprising the aad-12 event of the subject invention, wherein said method comprises the steps of: (a) sexually crossing a first parental soybean line (comprising an expression cassettes of the present invention, which confers said herbicideresistance trait to plants of said line) and a second parental soybean line (that lacks this herbicide tolerance trait) thereby producing a plurality of progeny plants; and (b) selecting a progeny plant by the use of the subject invention. Such methods may optionally comprise the further step of back-crossing the progeny plant to the second parental soybean line to producing a true-breeding soybean plant that comprises said herbicide tolerance trait.

According to some embodiments of the subject invention, methods of determining the zygosity of progeny of a cross are provided. Said methods can comprise contacting a sample, comprising soybean DNA, with a primer set of the subject invention. Said primers, when used in a nucleic-acid amplification reaction with genomic DNA from at least one of said soybean events, produce a first amplicon that is diagnostic for at least one of said soybean events. Such methods further comprise performing a nucleic acid amplification reaction, thereby producing the first amplicon; detecting the first amplicon; and contacting the sample comprising soybean DNA with said primer set, when used in a nucleic-acid amplification reaction with genomic DNA from soybean plants, produces a second amplicon comprising the native soybean genomic DNA homologous to the soybean genomic region; and performing a nucleic acid amplification reaction, thereby producing the second amplicon. The methods further comprise detecting the second amplicon, and comparing the first and second amplicons in a sample, wherein the presence of both amplicons indicates that the sample is heterozygous for the transgene insertion.

DNA detection kits using the compositions disclosed herein and methods well known in the art of DNA detection. The kits are useful for identification of the subject soybean event DNA in a sample and can be applied to methods for breeding soybean plants containing this DNA. The kits contain DNA sequences homologous or complementary to the amplicons, for example, disclosed herein, or to DNA sequences homologous or complementary to DNA contained in the transgene genetic elements of the subject events. These DNA sequences can be used in DNA amplification reactions or as probes in a DNA hybridization method. The kits may also contain the reagents and materials necessary for the performance of the detection method.

A "probe" is an isolated nucleic acid molecule which is attached to a conventional detectable label or reporter molecule (such as a radioactive isotope, ligand, chemiluminescent agent, or enzyme). Such a probe is complementary to a strand of a target nucleic acid, in the case of the present invention, to a strand of genomic DNA from one of said soybean events, whether from a soybean plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated/synthesized nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 polynucleotides or more in length. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods.

Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989. Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52 and 9.56-9.58. Accordingly, the nucleotide sequences of the invention may be used for their ability to selectively form duplex molecules with complementary stretches of DNA fragments.

Depending on the application envisioned, one can use varying conditions of hybridization to achieve varying degrees of selectivity of probe towards target sequence. For applications requiring high selectivity, one will typically employ relatively stringent conditions to form the hybrids, e.g., one will select relatively low salt and/or high temperature conditions, such as provided by about 0.02 M to about 0.15 M NaCl at temperatures of about 50° C. to about 70° C. Stringent conditions, for example, could involve washing the hybridization filter at least twice with high-stringency wash buffer (0.2×SSC, 0.1% SDS, 65° C.). Appropriate stringency conditions which promote DNA hybridization, for example, 6.0× sodium chloride/sodium citrate (SSC) at about 45° C., followed by a wash of 2.0×SSC at 50° C. are known to those skilled in the art. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well-known to those of skill in the art, and the teachings of U.S. Pat. Nos. 4,965,188 and 5,176,995 are exemplary of the methods of hybridization analyses.

In a particularly preferred embodiment, a nucleic acid of the present invention will specifically hybridize to one or more of the primers (or amplicons or other sequences) exemplified or suggested herein, including complements and fragments thereof, under high stringency conditions. In one aspect of the present invention, a marker nucleic acid molecule of the present invention has the nucleic acid sequence as set forth herein in one of the exemplified sequences, or complements and/or fragments thereof.

In another aspect of the present invention, a marker nucleic acid molecule of the present invention shares between 80% and 100% or 90% and 100% sequence identity with such nucleic acid sequences. In a further aspect of the present invention, a marker nucleic acid molecule of the present invention shares between 95% and 100% sequence identity with such sequence. Such sequences may be used as markers in plant breeding methods to identify the progeny of genetic crosses. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the soybean plant resulting from a sexual cross contains transgenic event genomic DNA from the soybean plant of the present invention, DNA extracted from a soybean plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, and/or the combined length of the primer pairs plus about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500, 750, 1000, 1250, 1500, 1750, 2000, or more nucleotide base pairs (plus or minus any of the increments listed above). Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA sequence. This distance can range from one nucleotide base pair up to about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202. PCR amplification methods have been developed to amplify up to 22 kb of genomic DNA. These methods as well as other methods known in the art of DNA amplification may be used in the practice of the present invention. The sequence of the heterologous transgene DNA insert or flanking genomic sequence from a subject soybean event can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. Agarose gel electrophoresis and staining with ethidium bromide is a common well known method of detecting DNA amplicons. Another such method is Genetic Bit Analysis where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

All patents, patent applications, provisional applications, and publications referred to or cited herein are incorporated by reference in their entirety to the extent they are not inconsistent with the explicit teachings of this specification.

The following examples are included to illustrate procedures for practicing the invention and to demonstrate certain preferred embodiments of the invention. These examples should not be construed as limiting. It should be appreciated by those of skill in the art that the techniques disclosed in the following examples represent specific approaches used to illustrate preferred modes for its practice. However, those of skill in the art should, in light of the present disclosure, appreciate that many changes can be made in these specific embodiments while still obtaining like or similar results without departing from the spirit and scope of the invention. Unless otherwise indicated, all percentages are by weight and all solvent mixture proportions are by volume unless otherwise noted.

The following abbreviations are used unless otherwise indicated.

AAD-12 aryloxyalkanoate dioxygenase-1
bp base pair
° C. degrees Celcius
DNA deoxyribonucleic acid
DIG digoxigenin
EDTA ethylenediaminetetraacetic acid
kb kilobase
μg microgram
μL microliter
mL milliliter M molar mass
OLP overlapping probe
PCR polymerase chain reaction
PTU plant transcription unit
SDS sodium dodecyl sulfate
SOP standard operating procedure
SSC a buffer solution containing a mixture of sodium chloride and sodium citrate, pH 7.0
TBE a buffer solution containing a mixture of Tris base, boric acid and EDTA, pH 8.3
V volts

EXAMPLES

Example 1

Event Specific Taqman Assay

An event specific TAQMAN ASSAY® was developed to detect the presence of soybean event DAS-68416-4 and to determine zygosity status of plants in breeding populations. To develop an event specific assay, specific Taqman primers and probes were designed according to the DNA sequences located in the 5' insert-to-plant junction. For specific detection of soybean event DAS-68416-4, a 128-bp DNA fragment that spans this 5' integration junction was amplified using two specific primers. The amplification of this PCR product was measured by a target-specific MGB probe synthesized by Applied Biosystems containing the FAM reporter at its 5'end. Specificity of this Taqman detection method for soybean event DAS-68416-4 was tested against 15 different aad-12 soybean events and non-transgenic soybean variety (Maverick) in duplex format with the soybean specific endogenous reference gene, lectin.

Example 1.1 gDNA Isolation gDNA samples of 15 different AAD-12 soybean events and non-transgenic soybean varieties were tested in this study. Genomic DNA was extracted using the Qiagen DNeasy 96 Plant Kit. Fresh soybean leaf discs, eight per sample, were used for gDNA extraction using a modified Qiagen DNeasy 96 Plant Kit protocol. The gDNA was quantified with the Pico Green method according to vendor's instructions (Molecular Probes, Eugene, Oreg.). Samples were diluted with DNase-free water resulting in a concentration of 10 ng/μL for the purpose of this study.

Example 1.2

Taqman Assay and Results

Specific Taqman primers and probes were designed for a soybean event DAS-68416-4 specific Taqman assay. These reagents can be used with the conditions listed below to detect aad-12 within soybean event DAS-68416-4. Table 1 lists the primer and probe sequences that were developed specifically for the detection of event DAS-68416-4.

TABLE 1

PCR Primers and Probes

| Name | Description | 5' to 3' sequence |
|---|---|---|
| Event Target Reaction | | |
| Soy416-F | Forward Primer | SEQ ID NO: 2 GGGCCTAACTTTTGGTGTGATG |
| Soy416-R | Reverse Primer | SEQ ID NO: 3 TACTTGCTCTTGTCGTAAGTCAATAAATT |
| Soy416-Probe | Probe | SEQ ID NO: 4 FAM-TTCAAGCACCAGTCAGCAT-MGB |
| Lectin Reference System Reaction | | |
| ZN_007 | Forward Primer | SEQ ID NO: 5 TCCCGAGTGGGTGAGGATAG |
| ZN_008 | Reverse Primer | SEQ ID NO: 6 TCATGCGATTCCCCAGGTAT |
| ZN_LT_002 | Probe | SEQ ID NO: 7 HEX-TTCTCTGCTGCCACGGGACTCGA-BHQ1 |

The multiplex PCR conditions for amplification are as follows: 1×PCR buffer, 0.5-2.5 mM $MgCl_2$, 0.2 mM dNTP, 0.2 μM Primer Soy416-F, 0.2 μM Primer Soy416-R, 0.2 μM Primer ZN_007, 0.2 μM Primer ZN_008, 0.08 μM Soy416-Probe, 0.08 uM ZN_LT_002, 40 U/mL HotStart Taq, 30 ng gDNA in a total reaction of 25 μl. The cocktail was amplified using the following conditions: i) 95° C. for 15 min., ii) 95° C. for 20 sec, iii) 60° C. for 60 sec, iv) repeat step ii-iii for 35 cycles, v) 4° C. hold. The Real time PCR was carried out on the BIO-RAD ICYCLER™ and ABI Gene Amp PCR System 9700 thermocyclers. Data analysis was based on measurement of the cycle threshold (CT), which is the PCR cycle number when the fluorescence measurement reaches a set value. CT value was calculated automatically by iCycler software.

The Taqman detection method for soybean event DAS-68416-4 was tested against 16 different aad-12 soybean events and non-transgenic soybean varieties in duplex format with soybean specific endogenous lectin as a reference gene. This assay specifically detected the soybean event DAS-68416-4 and did not produce or amplify any false-positive results from the controls (i.e. the 15 different aad-12 soybean events and non-transgenic soybean varieties). The event specific primers and probes can be used for the detection of the soybean event DAS-68416-4 and these conditions and reagents are applicable for zygosity assays.

The invention claimed is:

1. A method for determining event zygosity of a soybean plant comprising an AAD-12 soybean event pDAB4468-0416, said event comprising a transgene construct comprising an AAD-12 gene, said transgene construct being flanked by a 5' flanking soybean genomic DNA and a 3' flanking soybean genomic DNA, said method comprising:
  obtaining a DNA sample of genomic DNA from said soybean plant;
  producing a contacted sample by contacting said DNA sample with
    a. a first event primer and a second event primer, wherein said first event primer specifically binds said transgene construct, said second event primer specifically binds said 5' soybean genomic flanking DNA or said 3' soybean genomic flanking DNA, and wherein said first event primer and said second event primer produce an event amplicon when subjected to TAQMAN PCR conditions;
    b. a reference forward primer and a reference reverse primer that produce a reference amplicon from an endogenous soybean reference gene when subjected to TAQMAN PCR conditions;
    c. a florescent event probe that hybridizes with said event amplicon;
    d. a florescent reference probe that hybridizes with said reference amplicon;
  subjecting said contacted sample to fluorescence-based endpoint TAQMAN PCR conditions;
  quantitating said florescent event probe that hybridized to said event amplicon;
  quantitating said florescent reference probe that hybridized to said reference amplicon;
  comparing amounts of hybridized florescent event probe to hybridized florescent reference probe; and
  determining zygosity of pDAB4468-0416 by comparing florescence ratios of hybridized fluorescent event probe and hybridized fluorescent reference probe.

2. The method of claim 1 wherein said amplicons consist of 50-150 residues.

3. The method of claim 1 wherein said 5' flanking DNA comprises residues 1-2730 of SEQ ID NO:1, and said 3' flanking DNA comprises 9122-10,212 of SEQ ID NO:1.

4. The method of claim 1 wherein said transgene construct consists of residues 2731-9121 of SEQ ID NO:1.

5. The method of claim 1 wherein said reference gene is an endogenous soybean lectin gene.

6. The method of claim 1 wherein said second event primer binds residues 2530-2730 of SEQ ID NO:1 or the full complement of 2530-2730 of SEQ ID NO:1.

7. The method of claim 1 wherein said second event primer binds residues 9122-9322 of SEQ ID NO:1.

8. The method of claim 1 wherein said method is used for breeding introgression of the event into another soybean line.

9. The method of claim 8 wherein said another soybean line lacks said event.

10. The method of claim 1 wherein said amplicons consist of 100-200 basepairs.

11. The method of claim 1 wherein said reference gene comprises or hybridizes to a sequence selected from the group consisting of SEQ ID NO:5, SEQ ID NO:6, and SEQ ID NO:7.

12. The method of claim 1 wherein said reference primers comprise SEQ ID NO: 5 and SEQ ID NO:6, and said reference probe comprises SEQ ID NO:7.

13. The method of claim 1 wherein said probes are labeled with a fluorescent dye and quencher.

14. The method of claim 13 wherein said event probe comprises FAM as said fluorescent dye at the 5' end of said event probe and an MGB quencher on the 3' end of said event probe.

15. The method of claim 13 wherein said reference probe is labeled with HEX at the 5' end of said reference probe and a Black Hole Quencher 1 (BHQ1) at the 3' end of said reference probe.

16. The method of claim 1 wherein said event probe comprises SEQ ID NO:4.

17. The method of claim 1 wherein said event primers are selected from the group consisting of SEQ ID NO:2 and SEQ ID NO:3.

18. The method of claim 1 wherein results of said method are read directly in a plate reader.

19. The method of 1 wherein said DNA sample is obtained from a soybean plant in a field.

* * * * *

UNITED STATES PATENT AND TRADEMARK OFFICE
CERTIFICATE OF CORRECTION

PATENT NO. : 8,685,677 B2  
APPLICATION NO. : 13/511995  
DATED : April 1, 2014  
INVENTOR(S) : Stephen Novak et al.

Page 1 of 1

It is certified that error appears in the above-identified patent and that said Letters Patent is hereby corrected as shown below:

In the Claims

In Claim 6, Column 30, Line 25 after "of", insert --residues--.

Signed and Sealed this
Tenth Day of June, 2014

Michelle K. Lee
*Deputy Director of the United States Patent and Trademark Office*

SEQUENCE LISTING

<160> NUMBER OF SEQ ID NOS: 7

<210> SEQ ID NO 1
<211> LENGTH: 10212
<212> TYPE: DNA
<213> ORGANISM: Artificial Sequence
<220> FEATURE:
<223> OTHER INFORMATION: Insert and Flanking squences for Soybean Event

DAS-68416-4

<400> SEQUENCE: 1

```
ctgtcgttgg attcacagaa cattgacgcc agttttcact tcgttatctt tgaattcatt      60
aaaatcgaat ctctcaccta tacccccca tttttctaat ccatcataat caaaattcat     120
aaatgaatca gttaccatta ccataatacc ttttttgaaaa tgagtttgaa taatcagtat    180
ctttagaaaa ctaattaaga aattaaataa aaaatattta tcatgaagat gagtgtaaga    240
aaaattatga aagtataac tttatacatt tctataaaat tatttttct tttaatttct      300
taattaatat cctaagtaaa tgagttaata tttatctttc aaaaattctt atagtcgcca    360
attaattttc ccatgcaatg acaacttgtc cgtattctac gtggtaggtt aggctacctg    420
ccgagacaaa ttgccttgag acaaattcaa tagagaaccc ttccaaggga ccattataaa    480
tagagaactt tcattaaccg ataagccaca ccctttcaat caaacacaaa cacttgaagt    540
actaagttag tgtgtttgag caaattaact atggcttcgt tttgttctag attgacaatt    600
tgtttggctc tgtttgtcct catatggggg agtgccaatg cacaactttc tacaaacttt    660
tactaccatt catgtccaaa cctcttctcc tctgtgaaat ccacagtgca atctgccata    720
tctaaggaga cccgcatggg tgcttctctc cttcgcttgt tcttccacga ttgctttgtc    780
aatgtaattt atttgcacct tctcccactt acatacaaat atgctaagct tacatatagc    840
tcctctttct accacttgca tgcatcatct aattttgttt gaaacaacac ttgttccttt    900
tattatacac atcatctttg ataaaatttt gtcgtgtgca acttttttt agtgtgttaa     960
tcagttctat gatgatacta ttagttaaga aattttaatg cacttaataa accatttaa    1020
gtactttaac cgttcaatga tattatatat ttaaagataa taaatatttc tgcttttgtt   1080
tctatattag tgtagttaag aaccttctta cttcttagct agctaaatat taatgagtaa   1140
acattaacaa atgcagggat gtgatggttc aattctattg gatgacacat caagcttcac   1200
cggagagaag aacgcaaacc ccaacaggaa ctctgctcgt ggattcgagg ttattgacaa    1260
cattaaatca gccgtggaga agtgtgtcc aggagttgtt tcctgcgcag atatccttgc    1320
catcgctgcc agagactctg ttcagattgt aagtggtcaa acaaccaaca aaaacacatt    1380
aaactaaatc attaaattgt acatatcaaa attaattacc aatttagtac cacacatgca    1440
attaaagaga acattttgtt gattttgatc aatatagctt ggaggcccta catggaatgt    1500
taaacttgga agaagagacg ctagaactgc tagccaatct gctgctaaca atggcatccc    1560
tgcacccact tcaaaccta accaactcat ctcaagattt agcgctcttg gactttccac    1620
caaggacttg gtcgccttgt ccggtacaaa acatatatca cataattttc caattaatta   1680
catttcaatc atatagtaaa atttctcaat taattaggaa catgagaaac ttatagtcac   1740
acgttctttt gttgaggaat attgcatggt ttaattttgc tttcattagg tggtcacaca   1800
attgacaag caaggtgcac aaacttcaga gcccgcatct acaacgagac caacatagaa    1860
accgcatttg caaggactag gcagcaaagc tgccctagaa catcagggtc aggggacaac   1920
aatctggcac cacttgatct tcaaactcca accagctttg acaactacta cttcaagaac   1980
ctcgttcaga agaagggtct cctccactct gatcagcaac tgttcaacgg tgggtccacc   2040
gactccattg tgcgtggcta cagcaccaac ccgggcacct tctcctctga tttcgccgcc   2100
gccatgatca agatgggaga cattagtcct ctcactggct ccaatggaga aatcaggaag   2160
aattgtagaa ggattaacta atttgattca gtccttgaata ttaagggtcc tacacatacg   2220
caagcaattt aattgtgttt aataagttgt taaaacatgt tttggttgta ttttggattc   2280
```

```
ctagtgtagt ttcggtgatc aatgccgtct actttagtgt gttctacttc cctttatttt    2340
tgtttctttt ttacttttc cttaactata ttgtaggaaa aaaaaaatcc tttatcaagc    2400
atttatcaag aacggagttt gcttttaat tttcccttca taacattcca tcagaattca    2460
gttttgcttt tgcttctaaa ttacgttcaa atcaggatg ataatcggtt aggtaatata    2520
tacagtaccc cttgcatagt cacgtttgaa aaatataatc atacttagtt cggtaacaat    2580
ttaaattatc attctcgtaa tcattagcta cttatgcact catatccgta tccgctactt    2640
gctcttgtcg taagtcaata aattaatata aaaaaatact taaaacttgt tacaactaaa    2700 ttaaaattt atttttaaat cattcaagca ccagtcagca tcatcacacc aaaagttagg    2760
cccgaatagt ttgaaattag aaagctcgca attgaggtct acaggccaaa ttcgctctta    2820
gccgtacaat attactcacc ggatcctaac cggtgtgatc atgggccgcg attaaaaatc    2880
tcaattatat ttggtctaat ttagtttggt attgagtaaa acaaattcga accaaaccaa    2940
aatataaata tatagttttt atatatatgc ctttaagact ttttatagaa ttttctttaa    3000
aaaatatcta gaaatatttg cgactcttct ggcatgtaat atttcgttaa atatgaagtg    3060
ctccattttt attaaccttta ataattggt tgtacgatca ctttcttatc aagtgttact    3120
aaaatgcgtc aatctctttg ttcttccata ttcatatgtc aaaacctatc aaaattctta    3180
tatatctttt tcgaatttga agtgaaattt cgataattta aaattaaata gaacatatca    3240
ttatttaggt atcatattga tttttatact taattactaa atttggttaa ctttgaaagt    3300
gtacatcaac gaaaaattag tcaaacgact aaaataaata aatatcatgt gttattaaga    3360
aaattctcct ataagaatat tttaatagat catatgtttg taaaaaaat taatttttac    3420 taacacatat atttacttat caaaaatttg acaaagtaag attaaaataa tattcatcta    3480
acaaaaaaaa aaccagaaaa tgctgaaaac ccggcaaaac cgaaccaatc caaaccgata    3540
tagttggttt ggtttgattt tgatataaac cgaccaact cggtccattt gcacccctaa    3600
tcataatagc tttaatattt caagatatta ttaagttaac gttgtcaata tcctggaaat    3660
tttgcaaaat gaatcaagcc tatatggctg taatatgaat ttaaaagcag ctcgatgtgg    3720
tggtaatatg taatttactt gattctaaaa aaatatccca agtattaata atttctgcta    3780
ggaagaaggt tagctacgat ttacagcaaa gccagaatac aatgaaccat aaagtgattg    3840
aagctcgaaa tatacgaagg aacaaatatt tttaaaaaaa tacgcaatga cttggaacaa    3900
aagaaagtga tatattttt gttcttaaac aagcatcccc tctaaagaat ggcagttttc    3960
ctttgcatgt aactattatg ctcccttcgt tacaaaaatt ttggactact attgggaact    4020
tcttctgaaa atagtggcca ccgcttaatt aaggcgcgcc atgcccgggc aagcggccgc    4080
acaagtttgt acaaaaaagc aggctccgcg gtgactgact gaaaagcttg tcgacctgca    4140
ggtcaacgga tcaggatatt cttgtttaag atgttgaact ctatggaggt ttgtatgaac    4200
tgatgatcta ggaccggata agttcccttc ttcatagcga acttattcaa gaatgttttt    4260
gtgtatcatt cttgttacat tgttattaat gaaaaatat tattggtcat tggactgaac    4320
acgagtgtta aatatggacc aggcccccaaa taagatccat tgatatatga attaaataac    4380
aagaataaat cgagtcacca aaccacttgc cttttttaac gagacttgtt caccaacttg    4440
atacaaaagt cattatccta tgcaaatcaa taatcataca aaaatatcca ataacactaa    4500
aaaattaaaa gaaatggata atttcacaat atgttatacg ataaagaagt tactttttcca    4560 agaaattcac tgattttata agcccacttg cattagataa atggcaaaaa aaaacaaaaa    4620
ggaaaagaaa taaagcacga agaattctag aaaatacgaa atacgcttca atgcagtggg    4680
```

-continued

| | |
|---|---|
| acccacggtt caattattgc caattttcag ctccaccgta tatttaaaaa ataaaacgat | 4740 |
| aatgctaaaa aaatataaat cgtaacgatc gttaaatctc aacggctgga tcttatgacg | 4800 |
| accgttagaa attgtggttg tcgacgagtc agtaataaac ggcgtcaaag tggttgcagc | 4860 |
| cggcacacac gagtcgtgtt tatcaactca agcacaaat actttcctc aacctaaaaa | 4920 |
| taaggcaatt agccaaaaac aactttgcgt gtaaacaacg ctcaatacac gtgtcatttt | 4980 |
| attattagct attgcttcac cgccttagct ttctcgtgac ctagtcgtcc tcgtcttttc | 5040 |
| ttcttcttct tctataaaac aatacccaaa gcttcttctt cacaattcag atttcaattt | 5100 |
| ctcaaaatct taaaaacttt ctctcaattc tctctaccgt gatcaaggta aatttctgtg | 5160 |
| ttccttattc tctcaaaatc ttcgattttg ttttcgttcg atcccaattt cgtatatgtt | 5220 |
| ctttggttta gattctgtta atcttagatc gaagacgatt ttctgggttt gatcgttaga | 5280 |
| tatcatctta attctcgatt agggtttcat aaatatcatc cgatttgttc aaataatttg | 5340 |
| agttttgtcg aataattact cttcgatttg tgatttctat ctagatctgg tgttagtttc | 5400 |
| tagtttgtgc gatcgaattt gtcgattaat ctgagttttt ctgattaaca gagatctcca | 5460 |
| tggctcagac cactctccaa atcacaccca ctggtgccac cttgggtgcc acagtcactg | 5520 |
| gtgttcacct tgccacactt gacgatgctg gtttcgctgc cctccatgca gcctggcttc | 5580 |
| aacatgcact cttgatcttc cctgggcaac acctcagcaa tgaccaacag attacctttg | 5640 |
| ctaaacgctt tggagcaatt gagaggattg gcggaggtga cattgttgcc atatccaatg | 5700 |
| tcaaggcaga tggcacagtg cgccagcact ctcctgctga gtgggatgac atgatgaagg | 5760 |
| tcattgtggg caacatggcc tggcacgccg actcaaccta catgccagtc atggctcaag | 5820 |
| gagctgtgtt cagcgcagaa gttgtcccag cagttggggg cagaacctgc tttgctgaca | 5880 |
| tgagggcagc ctacgatgcc cttgatgagg caacccgtgc tcttgttcac caaaggtctg | 5940 |
| ctcgtcactc ccttgtgtat tctcagagca agttgggaca tgtccaacag gccgggtcag | 6000 |
| cctacatagg ttatggcatg acaccactg caactcctct cagaccattg gtcaaggtgc | 6060 |
| atcctgagac tggaaggccc agcctcttga tcggccgcca tgcccatgcc atccctggca | 6120 |
| tggatgcagc tgaatcagag cgcttccttg aaggacttgt tgactgggcc tgccaggctc | 6180 |
| ccagagtcca tgctcaccaa tgggctgctg gagatgtggt tgtgtgggac aaccgctgtt | 6240 |
| tgctccaccg tgctgagccc tgggatttca agttgccacg tgtgatgtgg cactccagac | 6300 |
| tcgctggacg cccagaaact gagggtgctg ccttggtttg agtagttagc ttaatcacct | 6360 |
| agagctcggt caccagcata attttttatta atgtactaaa ttactgtttt gttaaatgca | 6420 |
| attttgcttt ctcgggattt taatatcaaa atctatttag aaatacacaa tattttgttg | 6480 |
| caggcttgct ggagaatcga tctgctatca taaaaattac aaaaaaattt tatttgcctc | 6540 |
| aattatttta ggattggtat taaggacgct taaattattt gtcgggtcac tacgcatcat | 6600 |
| tgtgattgag aagatcagcg atacgaaata ttcgtagtac tatcgataat ttatttgaaa | 6660 |
| attcataaga aaagcaaacg ttacatgaat tgatgaaaca atacaaagac agataaagcc | 6720 |
| acgcacattt aggatattgg ccgagattac tgaatattga gtaagatcac ggaatttctg | 6780 |
| acaggagcat gtcttcaatt cagcccaaat ggcagttgaa atactcaaac cgccccatat | 6840 |
| gcaggagcgg atcattcatt gtttgttgg ttgccttttgc caacatggga gtccaaggtt | 6900 |
| gcggccgcgc gccgacccag ctttcttgta caaagtggtt gcggccgctt aattaaattt | 6960 |
| aaatgcccgg gcgtttaaac gcggccgctt aattaaggcc ggcctgcagc aaacccagaa | 7020 |
| ggtaattatc caagatgtag catcaagaat ccaatgttta cgggaaaaac tatggaagta | 7080 |

```
ttatgtaagc tcagcaagaa gcagatcaat atgcggcaca tatgcaacct atgttcaaaa    7140
atgaagaatg tacagataca agatcctata ctgccagaat acgaagaaga atacgtagaa    7200
attgaaaaag aagaaccagg cgaagaaaag aatcttgaag acgtaagcac tgacgacaac    7260
aatgaaaaga agaagataag gtcggtgatt gtgaaagaga catagaggac acatgtaagg    7320
tggaaaatgt aagggcggaa agtaaccttg tcacaaagga atcttatccc ccactactta    7380
tccttttata ttttccgtg tcattttgc ccttgagttt tcctatataa ggaaccaagt     7440
tcggcatttg tgaaaacaag aaaaaatttg gtgtaagcta ttttctttga agtactgagg    7500
atacaacttc agagaaattt gtaagttgt agatctccat gtctccggag aggagaccag     7560
ttgagattag gccagctaca gcagctgata tggccgcggt ttgtgatatc gttaaccatt    7620
acattgagac gtctacagtg aactttagga cagagccaca acaccacaa gagtggattg     7680 atgatctaga gaggttgcaa gatagatacc cttggttggt tgctgaggtt gagggtgttg    7740
tggctggtat tgcttacgct gggccctgga aggctaggaa cgcttacgat tggacagttg    7800
agagtactgt ttacgtgtca cataggcatc aaaggttggg cctaggatcc acattgtaca    7860
cacatttgct taagtctatg gaggcgcaag gttttaagtc tgtggttgct gttataggcc    7920
ttccaaacga tccatctgtt aggttgcatg aggctttggg atacacagcc cggggtacat    7980
tgcgcgcagc tggatacaag catggtggat ggcatgatgt tggttttggg caaagggatt    8040
ttgagttgcc agctcctcca aggccagtta ggccagttac ccagatctga ggtaccctga    8100
gcttgagctt atgagcttat gagcttagag ctcggatcca ctagtaacgg ccgccagtgt    8160
gctggaattc gcccttgact agataggcgc ccagatcggc ggcaatagct tcttagcgcc    8220
atcccgggtt gatcctatct gtgttgaaat agttgcggtg ggcaaggctc tctttcagaa    8280
agacaggcgg ccaaaggaac ccaaggtgag gtgggctatg gctctcagtt ccttgtggaa    8340
gcgcttggtc taaggtgcag aggtgttagc gggatgaagc aaaagtgtcc gattgtaaca    8400
agatatgttg atcctacgta aggatattaa agtatgtatt catcactaat ataatcagtg    8460
tattccaata tgtactacga tttccaatgt ctttattgtc gccgtatgta atcggcgtca    8520
caaaataatc cccggtgact ttcttttaat ccaggatgaa ataatatgtt attataattt    8580
ttgcgatttg gtccgttata ggaattgaag tgtgcttgcg gtcgccacca ctcccatttc    8640
ataattttac atgtatttga aaataaaaa tttatggtat tcaatttaaa cacgtatact     8700
tgtaaagaat gatatcttga agaaatata gtttaaatat ttattgataa aataacaagt     8760
caggtattat agtccaagca aaaacataaa tttattgatg caagtttaaa ttcagaaata    8820
tttcaataac tgattatatc agctggtaca ttgccgtaga tgaaagactg agtgcgatat    8880
tatggtgtaa tacatagcgg ccgggtttct agtcaccggt taggatccgt ttaaactcga    8940
ggctagcgca tgcacataga cacacacatc atctcattga tgcttggtaa taattgtcat    9000
tagattgttt ttatgcatag atgcactcga aatcagccaa ttttagacaa gtatcaaacg    9060
gatgtgactt cagtacatta aaaacgtccg caatgtgtta ttaagttgtc taagcgtcaa    9120 tatttttaatt cttaacaatc aatattttaa ttcttaaact ttattaaatc taacaataaa    9180
ctgtaagaac taattcttaa acttcaataa acaatactgc gttttagtaa ttaaattaat    9240
aatatataga tatagatata taatttgtca acatattctt acctattttt ccattgaaat    9300
atgttagcaa gttcaaaaaa agttttgaca aaaaactcta ctatcttttg tttcatttac    9360
tttatgtgag ggatataata gtaatataac atttagttta tttaaagaaa ataaaaaagt    9420
taatttctct ttctgccact gatactctat ggtggagaga tccgatgcag tggtggagcc    9480
```

-continued

```
tggcctcgac acataagtgt gacgacgcag ctgttgaaga gatctgattc gacggtgggg    9540
taatgcatgg tggttgacag gttgatgggt ggagaagacg taattgctac cgccgtcaac    9600
ggaggaagga gcaaagatgt ctcgtatgtg aaaattatgc ggttgagatg ccgtttcatt    9660
ccctttaaaa aaatcccttg atggttgcaa tgcaaattaa aaattgaaaa ataattaat     9720 tgttcaaatt aaagatttag catgaaaaaa aaaacactta attgtgccca tgactccatg    9780
acctgcgtaa cttgggaagg aaaggaattt ttttgctaaa ggaaggcatg ggaagatgag    9840
agaggagaga gaatcagtgg aagtgagaga aattaacttt ttgttttta aaaactaaat     9900 attatattac tattatatat atatatatat atatataaaa gatttttag ctggattctt     9960 gatataaaaa atttctcacc atatttatta ttatatattt ttttggagat ctcaaaaaag   10020
gaagttggat ttcttctcaa taactctaaa aaattattcc tatttcaaaa aatatttttt   10080
atgtctttct ctaattgatg aataatatct atttaagtat attttattgt gaaatccaca   10140
aaagtgactg ataaatctaa tttaggatct accattagag aaaaataaat aaattcttat   10200
attatatgtg at                                                       10212

<210> SEQ ID NO 2
<211> LENGTH: 22
<212> TYPE: DNA
<213> ORGANISM: Artificial Sequence
<220> FEATURE:
<223> OTHER INFORMATION: event primer

<400> SEQUENCE: 2
gggcctaact tttggtgtga tg                                                22

<210> SEQ ID NO 3
<211> LENGTH: 29
<212> TYPE: DNA
<213> ORGANISM: Artificial Sequence
<220> FEATURE:
<223> OTHER INFORMATION: event primer

<400> SEQUENCE: 3
tacttgctct tgtcgtaagt caataaatt                                         29

<210> SEQ ID NO 4
<211> LENGTH: 19
<212> TYPE: DNA
<213> ORGANISM: Artificial Sequence
<220> FEATURE:
<223> OTHER INFORMATION: event probe

<400> SEQUENCE: 4
ttcaagcacc agtcagcat                                                    19

<210> SEQ ID NO 5
<211> LENGTH: 20
<212> TYPE: DNA
<213> ORGANISM: Artificial Sequence
<220> FEATURE:
<223> OTHER INFORMATION: Lectin Reference primer

<400> SEQUENCE: 5
tcccgagtgg gtgaggatag                                                   20

<210> SEQ ID NO 6
<211> LENGTH: 20
<212> TYPE: DNA
<213> ORGANISM: Artificial Sequence
<220> FEATURE:
```

-continued

```
<223> OTHER INFORMATION: Lectin Reference primer

<400> SEQUENCE: 6
tcatgcgatt ccccaggtat                                                    20

<210> SEQ ID NO 7
<211> LENGTH: 23
<212> TYPE: DNA
<213> ORGANISM: Artificial Sequence
<220> FEATURE:
<223> OTHER INFORMATION: Lectin Reference probe

<400> SEQUENCE: 7
ttctctgctg ccacgggact cga                                                23
```